United States Patent
Katou et al.

(10) Patent No.: US 7,672,878 B2
(45) Date of Patent: Mar. 2, 2010

(54) CONSUMABLES SUPPLY SYSTEM

(75) Inventors: Shigeru Katou, Kyoto (JP); Takeshi Matsuda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1333 days.

(21) Appl. No.: 10/362,750

(22) PCT Filed: Aug. 29, 2001

(86) PCT No.: PCT/JP01/07415

§ 371 (c)(1),
(2), (4) Date: May 12, 2003

(87) PCT Pub. No.: WO02/19193

PCT Pub. Date: Mar. 7, 2002

(65) Prior Publication Data

US 2003/0172009 A1    Sep. 11, 2003

(51) Int. Cl.
*G06Q 10/00* (2006.01)
*G06G 1/14* (2006.01)
*G06F 17/00* (2006.01)

(52) U.S. Cl. .......................... 705/28; 705/22; 700/236
(58) Field of Classification Search ............... 705/28
See application file for complete search history.

(56) References Cited

U.S. PATENT DOCUMENTS 5,305,199 A * 4/1994 LoBiondo et al. ............ 705/28
H1743 H * 8/1998 Graves et al. ............... 700/236
6,023,593 A  2/2000 Tomidokoro
6,085,493 A  7/2000 DeBusk et al.

FOREIGN PATENT DOCUMENTS

| EP | 0 715 221 | 6/1996 |
|----|-----------|--------|
| JP | 64-44851 | 2/1989 |
| JP | 7-194559 | 8/1995 |
| JP | 8-187921 | 7/1996 |
| JP | 8-263562 | 10/1996 |
| JP | 10-87036 | 4/1998 |
| JP | 11-45304 | 2/1999 |
| JP | 11-345267 | 12/1999 |
| JP | 2000-194767 | 7/2000 |
| WO | 99/15990 | 4/1999 |

* cited by examiner

*Primary Examiner*—F. Zeender
*Assistant Examiner*—Faris Almatrahi
(74) *Attorney, Agent, or Firm*—Hamre, Schumann, Mueller & Larson, P.C.

(57) ABSTRACT

In a consumables supply management system in which clinical test analysis devices (1) in medical institutions (A, B, . . . ) and a computer (2) of a consumables supplier (C) are connected via a communications line (10), operation status data including information on the status of consumption of the consumables in the clinical test analysis device (1) are transmitted to the computer (2) via the communications line (10). The computer (2) has previously stored data on the inventory of consumables in each medical institution, and determines the quantity of consumables consumed in each medical institution based on the operation status data that are received, updates the consumables inventory data, and if necessary, carries out the procedures for supplying an appropriate quantity of consumables.

17 Claims, 12 Drawing Sheets

|  | Measurement Date and Time | Test Strip Type | Measurements | LOT Number |
|---|---|---|---|---|
| d1 → | 2000/5/10 9:52 | GPT | 1 | BR8J16 |
| d2 → | 2000/5/10 9:52 | GOT | 1 | BQ9E19 |
| d3 → | 2000/5/10 10:25 | GPT | 1 | BR8J16 |
| d4 → | 2000/5/10 10:25 | GOT | 1 | BQ9E19 |
| d5 → | 2000/5/10 11:32 | GPT | 1 | BR8J16 |
| d6 → | 2000/5/10 11:32 | GOT | 1 | BQ9E19 |
| d7 → | 2000/5/10 11:45 | GLU | 1 | BF0D28 |
| d8 → | 2000/5/10 12:02 | GLU | 1 | BF0D28 |
| d9 → | 2000/5/10 13:01 | Screening 1 | 1 | MA9E03 |
| d10 → | 2000/5/11 9:25 | GPT | 1 | BR8J16 |
| d11 → | 2000/5/11 10:35 | GOT | 1 | BQ9E19 |
| d12 → | 2000/5/11 11:12 | GLU | 1 | BF0D28 |
| d13 → | 2000/5/11 11:30 | GLU | 1 | BF0D28 |

FIG. 7

| Measurement Date | Test Strip Type | Measurements | Test Strips Consumed | Tips Consumed | Specimen Containers Consumed | Management Samples Consumed |
|---|---|---|---|---|---|---|
| 2000/5/10 | GOT | 3 | 3 | 3 | 3 | - |
| 2000/5/10 | GPT | 3 | 3 | - | - | - |
| 2000/5/10 | GLU | 2 | 2 | 2 | 2 | - |
| 2000/5/10 | Screening 1 | 1 | 1 | 1 | 1 | - |
| 2000/5/11 | GOT | 1 | 1 | 1 | 1 | - |
| 2000/5/11 | GPT | 1 | 1 | 1 | 1 | - |
| 2000/5/11 | GLU | 2 | 2 | 2 | 2 | - |

FIG. 9

CONSUMABLES SUPPLY SYSTEM

TECHNICAL FIELD

The present invention relates to consumables supply management systems for supplying appropriate quantities of consumables at appropriate times to measurement devices that use consumables, such as clinical test analysis devices.

BACKGROUND ART

Conventionally, clinical test measurement devices have been used widely in medical institutions, for example. Among the conventional clinical test measurement devices there are devices having a communication function allowing them to transmit, for example, data to computers. Systems are also known in which data or the like are obtained through a measurement device connecting to a personal computer or a host computer, for example, inside a medical institution or connecting to a computer outside a medical institution via a public network or the like such as a telephone line, and gathered in a computer and processed.

A clinical test measurement device carries out measurement using reagents (including test paper and test strips), however, because these are disposable, it was necessary for a user of a clinical test analysis device to manage the inventory and the amount of consumption of these consumables and, predicting when the stock would run out, place purchase orders for an appropriate quantity of consumables at appropriate times.

However, there was the problem of consumables not being supplied in time due to forgetting to place an order or an inadequate transmission of information regarding consumable usage, for example, and this impeded the task of measurement. Also, because reagent makers and consumable suppliers such as wholesales deliver products after an order has been placed by a user of an analysis device, there is the problem that it is necessary for them to secure excess stock in order to prevent running out of items, and this increases their distribution costs.

The present invention was arrived at in order to solve these problems, and it is an object thereof to provide a consumables supply management system that both allows a required and sufficient stock of consumables to be always secured, even if a user of a measurement device does not, for example, manage the inventory of and place orders for consumables, and also allows consumables suppliers to reduce their distribution costs through the optimization of their inventory quantity.

DISCLOSURE OF THE INVENTION

In order to achieve the above object, a consumables supply management device of the present invention is connected via a communications line to a measurement device using consumables and manages the supply of consumables to a user of the measurement device, where operation status data including information on a consumption status of consumables is generated in the measurement device. The consumables supply management device includes an inventory data memory portion for storing consumables inventory data including information on an inventory status of consumables in a user of the measurement device, a data reception portion for receiving the operation status data from the measurement device via the communications line, a data processing portion that determines a quantity of consumables consumed by the measurement device based on the operation status data received by the data reception portion, and updates the consumables inventory data in the inventory data memory portion, and a supply determining portion for determining whether it is necessary to supply consumables to the user of the measurement device based on the consumables inventory data updated by the data processing portion.

With this configuration, the consumables supply management device receives information on the status of consumption of consumables in a measurement device via a communications line, and based on this information updates data on the inventory status of the consumables and determines whether it is necessary to supply the consumables.

Thus, it is possible to provide a consumables supply management device with which it is easy for consumables suppliers to predict the demand for consumables, and thus easily can set production schedules and lower distribution costs through optimization of their inventory. There is the additional benefit that consumables suppliers can use the consumables supply management device to manage the supply of consumables reliably, so that users of the management device always can maintain a required and a sufficient stock of consumables without managing the inventory of or placing orders for consumables, for example, and measurement is not impeded by inventory shortages.

It is preferable that the consumables supply management device further includes a supply processing portion that carries out a procedure for supplying consumables to the user if the supply determining portion determines that it is necessary to supply those consumables.

With this configuration, the supplier of consumables is spared the effort of performing the procedure for supplying consumables to users, allowing the supply of consumables to be managed more efficiently.

In the consumables supply management device it is preferable that a required inventory quantity of the consumables in the user of the measurement device is predetermined, and that the supply determining portion determines whether it is necessary to supply consumables to the user of the measurement device by comparing an inventory quantity of the consumables updated by the data processing portion and the required inventory quantity.

With this configuration, by suitably determining in advance the inventory of consumables that is required in a user of the measurement device, new consumables can be supplied before the stock of consumables runs out and problems such as excess inventory, or conversely, impediments to measurement caused by inventory shortages can be avoided.

In the consumables supply management device it is preferable that the supply processing portion sets the quantity of consumables supplied to the user to a quantity predetermined for that user.

With this configuration, by suitably setting in advance the quantity of consumables to be supplied to users, a predetermined quantity of consumables always can be supplied when stock has run low. Accordingly, there is the benefit that users easily can manage their inventory because the quantity of consumables that is supplied each time is known in advance, and consumables suppliers easily can set their production schedules, for example.

In the consumables supply management device it is preferable that the supply processing portion determines the quantity of consumables supplied to the user from a record of consumption of the consumables by that user.

With this configuration, by suitably setting the quantity of consumables that should be supplied at one time in accordance with the record of consumption of consumables by each user, it is for example possible to eliminate unnecessary waste, such as unused consumables expiring for users with low consumption.

In the consumables supply management device it is preferable that the supply processing portion determines the quantity of consumables supplied to the user in correspondence with temporal fluctuations in the quantity of the consumables that are consumed.

With this configuration, it is for example possible to increase the quantity of consumables for health examinations during periods in which many health examinations are performed, thereby allowing a suitable quantity of consumables to be supplied in correspondence with user demand and allowing the stock of consumables to be optimized.

In the consumables supply management device it is preferable that in the case where the supply processing portion carries out a procedure for supplying the same type of consumable to a plurality of users, the procedures are performed so that a lot having a closer expiration date is supplied to a user that consumes a larger quantity of the consumable rather than to a user that consumes a smaller quantity.

With this configuration, in the case where a procedure for supplying the same type of consumable to a plurality of users are performed, a lot with a closer expiration date is supplied to a user where the consumption of that consumable is greatest, thereby eliminating wasted products caused by consumables expiring unused.

In the consumables supply management device it is preferable that the consumables used by the measurement device include a specimen consumable, one unit of which is used per specimen, that the operation status data include a measurement time for each measurement, and that when a difference in the measurement times of a plurality of measurements is within a predetermined time, the data processing portion determines that the plurality of measurements are measurements in which an identical specimen was used, and regards the quantity of the specimen consumables consumed for the plurality of measurements as the single unit. It is also preferable that a single unit of the specimen consumable includes at least one of a specimen container and a sampling tip.

With this configuration, it is possible to determine accurately the quantity of specimen consumables that are consumed when, for example, a plurality of items are measured by applying drops of a sample that has been taken from a single specimen to a plurality of test strips, even if a single specimen is measured more than once.

In order to achieve the objects mentioned above, a consumables supply management system of the present invention is a system in which a measurement device that uses consumables and a consumables supply management device for managing supply of consumables to a user of the measurement device are connected via a communications line, where the measurement device includes an operation status memory portion for storing operation status data including information on a consumption status of the consumables and a data transmission portion for transmitting the operation status data to the consumables supply management device via the communications line, and where the consumables supply management device includes an inventory data memory portion for storing consumables inventory data including information on an inventory status of consumables in a user of the measurement device, a data reception portion for receiving the operation status data from the measurement device via the communications line, a data processing portion that determines a quantity of consumables consumed by the measurement device based on the operation status data received by the data reception portion, and updates the consumables inventory data in the inventory data memory portion, and a supply determining portion for determining whether it is necessary to supply consumables to the user of the measurement device based on the consumables inventory data updated by the data processing portion.

With this system, the measurement device transmits information on the status of consumption of the consumables to the consumables supply management device, whereas the consumables supply management device receives this information and based on this updates the data on the inventory of the consumables, and then determines whether it is necessary to supply consumables to the user of the measurement device based on the updated inventory data.

Thus, it is possible to provide a consumables supply management system with which it is easy for consumables suppliers to predict the demand for consumables, and thus easily can set production schedules and lower distribution costs through optimization of their inventory. Also, users of the management device can maintain a required and a sufficient stock of consumables from the supplier of the consumables without managing the inventory of or placing orders for consumables, for example, and measurement is not impeded by inventory shortages.

In the consumables supply management system it is preferable that the consumables supply management device further includes a supply processing portion that carries out a procedure for supplying consumables to the user if the supply determining portion determines that it is necessary to supply consumables.

With this configuration, the supplier of consumables can be spared the effort of performing the procedure for supplying consumables to users, allowing the supply of consumables to be managed more efficiently.

In the consumables supply management system it is preferable that a required inventory quantity of consumables in the user of the measurement device is predetermined, and that the supply determining portion of the consumables supply management device determines whether it is necessary to supply consumables to the user of the measurement device by comparing an inventory quantity of the consumables updated by the data processing portion and the required inventory quantity.

With this system, by suitably determining in advance the inventory of consumables that is required in a user of the measurement device, new consumables can be supplied before the stock of consumables runs out and problems such as excess inventory, or conversely, impediments to measurement caused by inventory shortages can be avoided.

In the consumables supply management system it is preferable that the supply processing portion of the consumables supply management device sets the quantity of consumables supplied to the user to a quantity predetermined for that user;

With this system, by suitably setting in advance the quantity of consumables to be supplied to users, a predetermined quantity of consumables always can be supplied when stock has run low. Accordingly, there is the benefit that users easily can manage their inventory because the quantity of consumables that is supplied each time is known in advance, and consumables suppliers easily can set their production schedules, for example.

In the consumables supply management system it is preferable that the supply processing portion of the consumables supply management device determines the quantity of consumables supplied to the user from a record of consumption of the consumables by that user.

With this system, by suitably setting the quantity of consumables that should be supplied at one time in accordance with the record of consumption of consumables by each user, it is for example possible to eliminate unnecessary waste, such as unused consumables expiring for users with low consumption.

In the consumables supply management system it is preferable that the supply processing portion of the consumables supply management device determines the quantity of consumables supplied to the user in correspondence with temporal fluctuations in the quantity of the consumable that is consumed, and allows inventory of the consumables to be optimized.

With this configuration, it is for example possible to increase the quantity of consumables for health examinations during periods in which many health examinations are performed, thereby allowing a suitable quantity of consumables to be supplied in correspondence with user demand and allowing the stock of consumables to be optimized.

In the consumables supply management system it is preferable that in the case where the supply processing portion of the consumables supply management device carries out a procedure for supplying the same type of consumable to a plurality of users, the procedure is performed so that a lot having a closer expiration date is supplied to a user that consumes a larger quantity of the consumable rather than a user that consumes a smaller quantity.

With this system, in the case where a procedure for supplying the same type of consumable to a plurality of users are performed, a lot with a closer expiration date is supplied to a user where the consumption of that consumable is greater, thereby eliminating wasted products caused by consumables expiring unused.

In the consumables supply management system it is preferable that the consumables used by the measurement device include a specimen consumable, one unit of which is used per specimen, that the operation status data include a measurement time for each measurement, and that when a difference in the measurement times of a plurality of measurements is within a predetermined time, the data processing portion determines that the plurality of measurements are measurements in which an identical specimen was used, and regards the quantity of the specimen consumables consumed in the plurality of measurements as the one unit. Also, it is preferable that one unit of the specimen consumable includes at least one of a specimen container and a sampling tip.

With this system, it is possible to determine accurately the quantity of specimen consumables that are consumed when, for example, a plurality of items are measured by applying drops of a sample that has been taken from a single specimen to a plurality of test strips, even if a single specimen is measured more than once.

To achieve the above objects, a measurement device of the present invention is a measurement device that uses consumables, that is connected via a communications line to a consumables supply management device, which manages supply of the consumables in correspondence with a consumption status of the consumables, and that includes an operation status memory portion for storing operation status data including information on a consumption status of the consumables, and a data transmission portion for transmitting the operation status data to the consumables supply management device via the communications line.

With this configuration, the status of consumption of consumables by the measurement device is transmitted to the consumables supply management device via a communications line, and the consumables supply management device manages the supply of consumables based on the information on the status of consumption that is received. Thus, it is possible to provide a measurement device with which it is not necessary for a user to manage the inventory of consumables.

To achieve the above objects, a program storage medium according to the present invention is a storage medium on which is stored a program for controlling the operation of a consumables supply management device that is connected via a communications line to a measurement device using consumables and that manages the supply of consumables to a user of the measurement device, the program executing the processes of providing, in the consumables supply management device, an inventory data memory portion for storing consumables inventory data including information on an inventory status of consumables in a user of the measurement device, creating, in the measurement device, operation status data including information on a consumption status of consumables, receiving the operation status data from the measurement device via the communications line, determining a consumed quantity of consumables in the measurement device based on the operation status data that are received, updating the consumables inventory data in the inventory data memory portion based on the consumed amount, and carrying out procedures for supplying consumables to the user if it is determined that it is necessary to supply those consumables to the user of the measurement device based on the updated consumables inventory data.

Thus, by executing the recorded program on a CPU, for example, it is possible to realize a consumables supply management device with which users of the management device always can maintain a required and a sufficient stock of consumables without managing the inventory of or placing orders for consumables, for example, and with which suppliers of the consumables can lower their distribution costs by optimizing their inventory of consumables.

BRIEF DESCRIPTION OF THE DRAWINGS

FIG. 7 is a diagram showing an example of operation status data of the clinical test analysis device.

FIG. 9 is a diagram showing the quantity of consumables consumed by the clinical test analysis device that is calculated in the computer.

BEST MODE FOR CARRYING OUT THE INVENTION

First Embodiment

Hereinafter, an embodiment of the present invention is described with reference to the drawings.

It is an object of the consumables supply system according to this embodiment to adequately supply consumables used by clinical test analysis devices to medical institutions and the like in which clinical test analysis devices are used.

Figure 1:
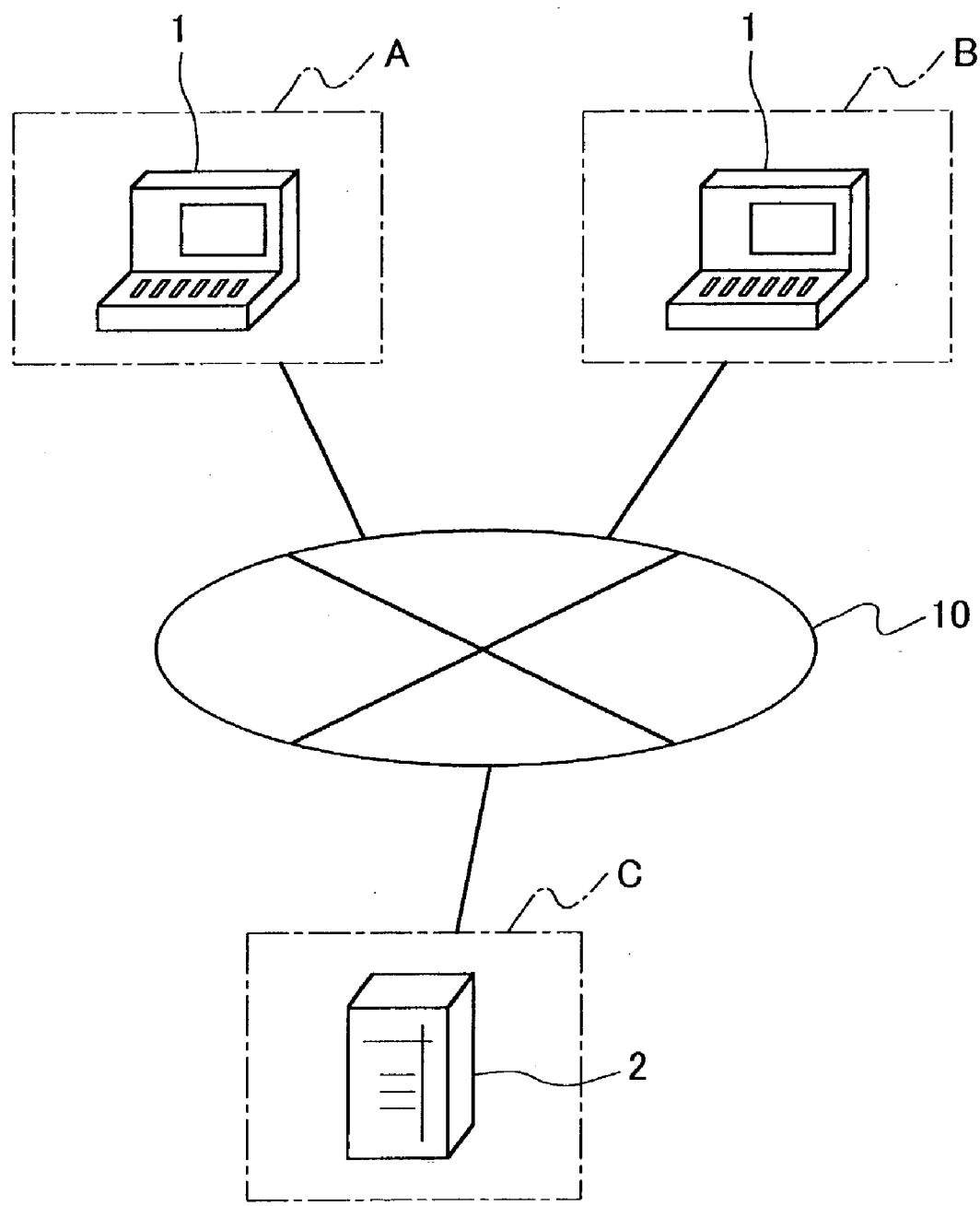
FIG. 1 is a block diagram showing the configuration of a consumables supply management system according to an embodiment of the invention.

To achieve this, as shown in FIG. 1, in this consumables supply system, clinical test analysis devices 1, which are set up and used in medical institutions A, B, . . . , are connected to a computer 2 (consumables supply management device) of a consumables supplier C via a communications line 10. It should be noted that the consumables supplier C can be the manufacturer of the clinical test analysis devices 1 mentioned above, a manufacture of the consumables, a wholesales, or any other party apart from these three.

The clinical test analysis devices 1 in the medical institutions accumulate information on consumables usage and transmit this information to the computer 2 via the communications line 10. The computer 2 determines the quantity of consumables remaining in each medical institution and carries out procedures for shipping the consumables before the stock of consumables is depleted.

By doing this, not only is the effort for managing the inventory of and placing orders for consumables in the medical institutions A, B, . . . using the clinical test analysis devices 1 obviated, but the consumables supplier C can reduce their excess stock and lower distribution costs.

The configuration and the operation of this consumables supply system is described in detail below.

First, the clinical test analysis devices 1 are described.

The clinical test analysis devices 1 are capable of testing a plurality of items using single test strips and multiple test strips, which are described later, in the same way as the conventional automated clinical chemical analyzer manufactured by Arkray, Inc. (product name Spotchem, model number SP-4420).

In addition to the test strips mentioned above, the consumables that are used by the clinical test analysis devices 1 include management samples used during calibration, specimen containers, and tips used when sampling a specimen from a specimen container, and these are supplied from the consumables supplier C.

There are two types of test strips used by the clinical test analysis devices 1: single test strips for measuring a single item and multiple test strips, in which test paper pads for two to six items are provided on a single test strip. Because a multiple test strip consolidates test paper pads for a maximum of six items on a single test strip to correspond to the application, it allows test data for all required items to be obtained through a single measurement, and has excellent cost performance. Consequently, when carrying out a test with a clinical test analysis device 1, a single test strip or a multiple test strip is selected and used in accordance with the application and objective.

For example, in a case where a patient visits a hospital for a specific ailment, normally it is sufficient to test for only a specific item. For example, if the patient is a diabetic, then a test is performed using a single test strip for GLU, and if the patient has weakened liver function, then a single test strip for GOT or a single test strip for GPT is used.

On the other hand, when a patient is examined for the first time, it is effective to use a multiple test strip for a general screening, on which test paper pads for the six items GPT, GOT, BUN, GLU, T-Cho, and T-Bil are provided, to test for six items at once.

There are various other possibilities for the multiple test strips provided by the consumables supplier C, such as multiple test strips for testing liver function (six items: LDH, Alb, GPT, GOT, T-Pro, and T-Bil), for testing renal function (five items: CRE, Alb, T-Pro, UA, and BUN), and for testing circulatory function (six items: LDH, CPK, GOT, T-Pro, BUN, and T-Cho).

It should be noted that with the clinical test analysis devices 1 it is possible to simultaneously test six single test strips and one multiple test strip, so that at one time a single specimen can be profiled for up to twelve items.

Here, the functional configuration of this clinical test analysis device is described with reference to FIG. 2.

Figure 2:
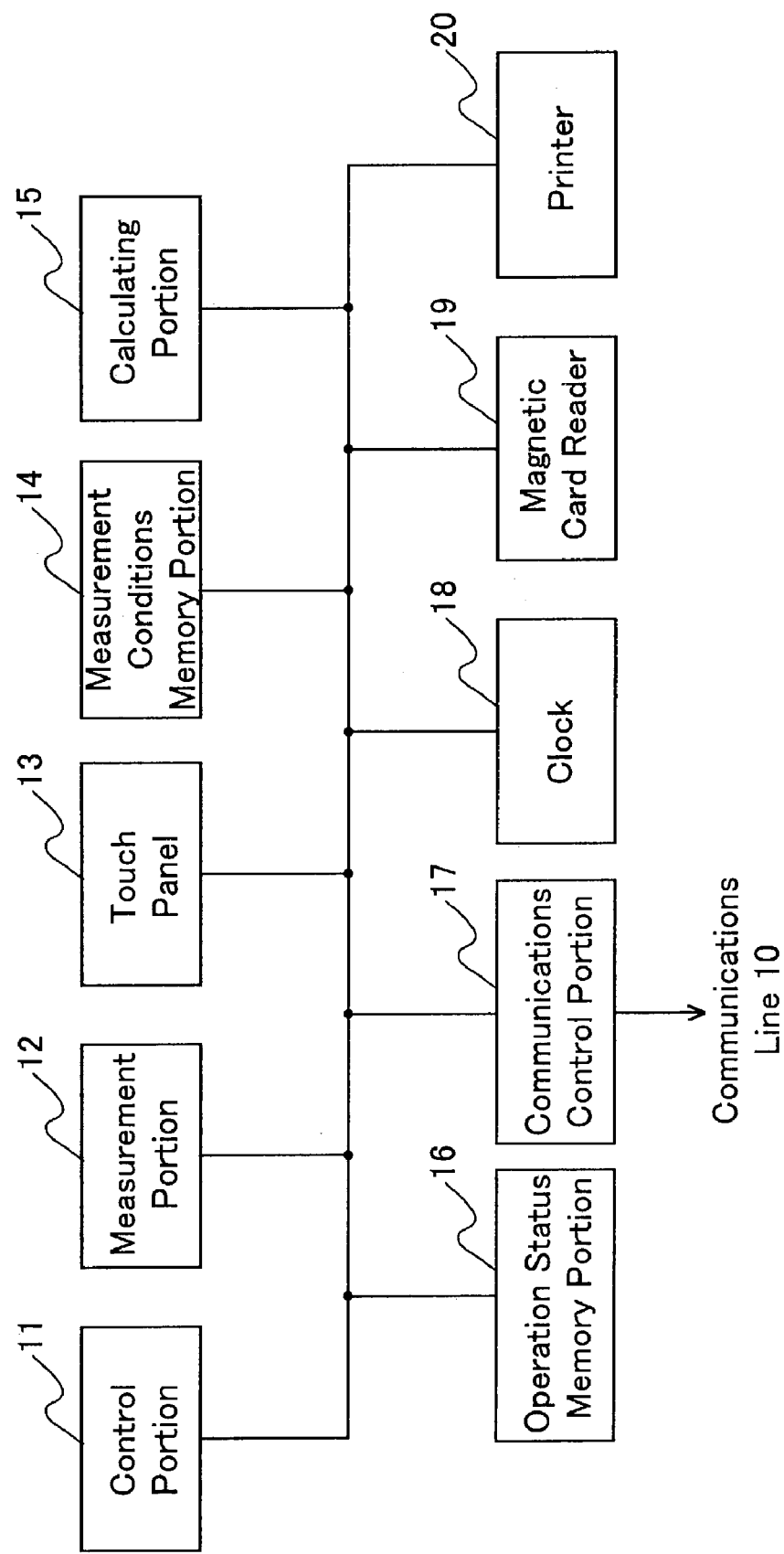
FIG. 2 is a block diagram showing the configuration of the clinical test analysis device in the consumables supply management system.

As shown in FIG. 2, the clinical test analysis device 1 is provided with a control portion 11, a measurement portion 12, a touch panel 13, a measurement conditions memory portion 14, a calculating portion 15, an operation status memory portion 16, a communications control portion 17, a clock 18, a magnetic card reader 19, and a printer 20.

The control portion 11 is made of a CPU or the like, and controls the overall operation of the clinical test analysis device 1. The measurement portion 12 is provided with a test strip mount, a specimen container mount, a tip cartridge mount, a sampling nozzle, and a photometric portion, and performs measurement.

The test strip mount of the measurement portion 12, as mentioned above, is configured so that six single test strips and one multiple test strip can be set thereon. The specimen container mount is configured so that a specimen container can be set thereon.

The sampling nozzle is configured so that a disposable tip is mounted to the tip of the nozzle for each specimen in order to avoid contamination between specimens. The sampling nozzle sucks in the specimen from the specimen container and places a drop thereof onto the test paper pads of the test strip. It should be noted that the mounting of the tips is automated.

A tip cartridge provided with is set onto the tip cartridge mount. The tips are disposable, and once a drop of the specimen has been placed on the test strip, the tips are automatically returned to the tip cartridge by the sampling nozzle and the entire tip cartridge is disposed of after testing is over.

Thus, because the mounting and removal of tips to and from the sampling nozzle is automated, the operator does not have to directly touch the tip himself, protecting him from infection.

The photometric portion irradiates light of a wavelength corresponding to the measured item on a test strip on which a drop of the specimen has been placed, and by measuring the light that is reflected, detects the concentration, for example, of that item. In the case of a multiple test strip, measurement is carried out by making light of wavelengths corresponding to each of the measured items incident on the test paper pads of the measured items on the test strip.

The touch panel 13 is made of a liquid crystal panel or the like, and both displays operator commands, for example, and can be operated by the operator pressing an object displayed on the screen with his finger. The measurement conditions memory portion 14 records the measurement conditions, that is, the operation procedure of the sampling nozzle and the wavelength of the test light that is used by the photometric portion, for example, for each measured item. The calculating portion 15 performs correction calculation, for example, for the measurement data that are obtained by the measurement portion 12.

The operation status memory portion 16 records the date and time of measurement, the items measured, and the number of measurements as the measurement status for all the measurements performed by the clinical test analysis device 1. The communications control portion 17 communicates with the computer 2, which is owned by the consumables supplier C, via the communications line 10, which is a telephone network, for example. The clock 18 is provided for obtaining the date and time of measurement, for example. The printer 20 prints out test results, for example.

The magnetic card reader 19 is provided for inputting calibration information, for example, to the device. It should be noted that calibration information is stored on a magnetic card created for each lot of test strips by the maker supplying the test strips, and the magnetic card is shipped along with the test strips. Thus, when the lot number of the test strips that are used changes, then the user of the clinical test analysis device 1 can carry out calibration through the simple operation of using the magnetic card reader 19 to read out the calibration information from the magnetic card that is packaged along with the new test strips to be used.

Next, the functional configuration of the computer 2 is described.

Figure 3:
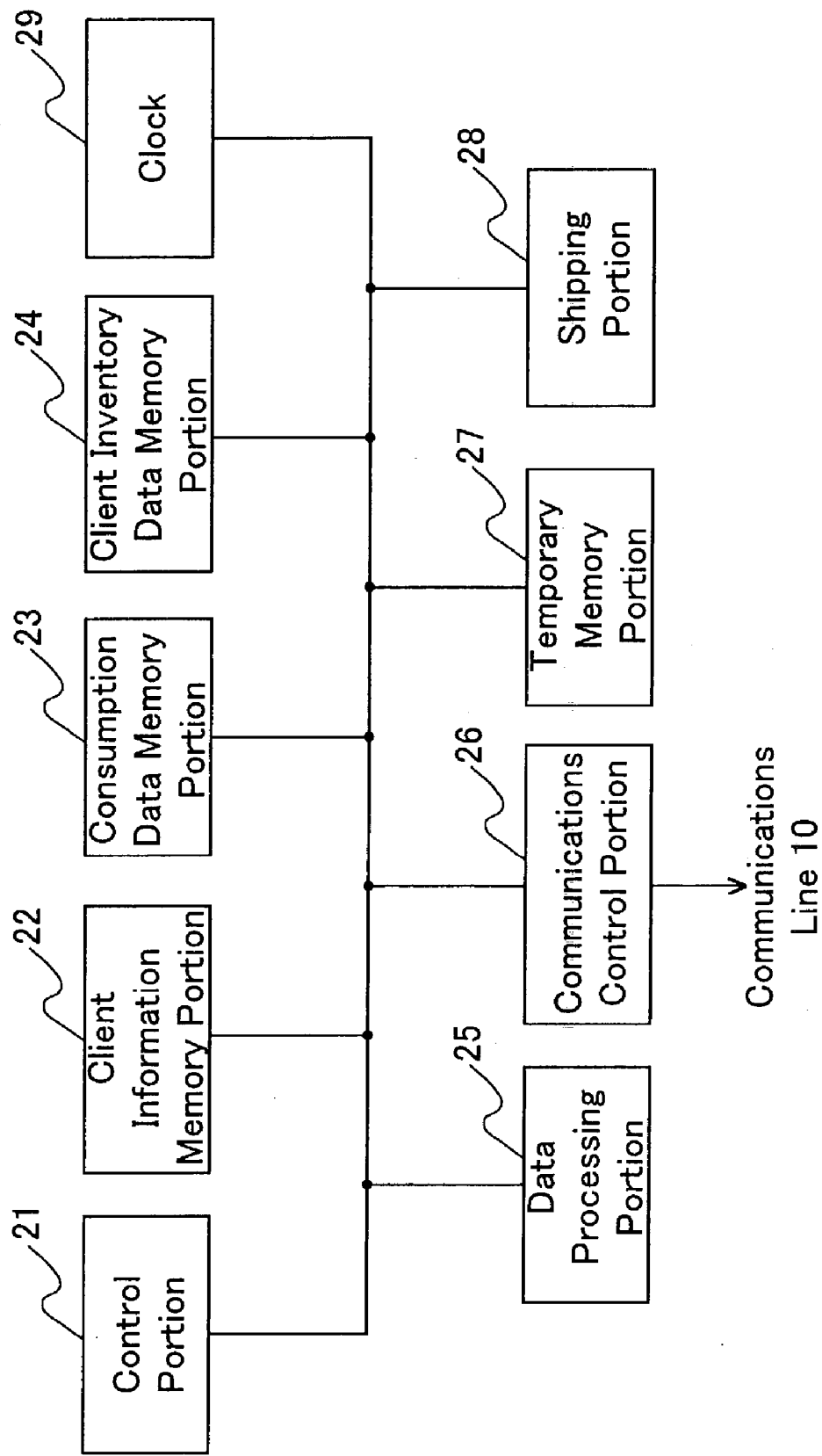
FIG. 3 is a block diagram showing the configuration of the computer of the consumables supplier in the consumables supply management system.

As shown in FIG. 3, the computer 2 is provided with a control portion 21, a client information memory portion 22, a consumption data memory portion 23, a client inventory data memory portion 24, a data processing portion 25, a communications control portion 26, a temporary memory portion 27, a shipping portion 28, and a clock 29.

The control portion 21 controls the overall operation of the computer 2. The communications control portion 26 connects to the clinical test analysis devices 1 in each medical institution via the communications line 10, and sends and receives data, for example. The temporary memory portion 27 is provided for temporarily storing data or the like that have been received by the communications control portion 26.

The client information memory portion 22 stores various types of information on the medical institutions using the clinical test analysis devices 1, such as their address when communicating over the communications line 10 (for example, a telephone number or an electronic-mail address) or their postal address, for example. The data processing portion 25, which is described in greater detail later, calculates the consumption and the inventory of consumables in each medical institution based on the information that is transmitted from the clinical test analysis devices 1 in each medical institution.

The consumption data memory portion 23 stores the number of the consumables that are consumed, for example, in each medical institution, which is calculated by the data processing portion 25. The client inventory data memory portion 24 stores the number, for example, of the consumables in each medical institution, which is calculated by the data processing portion 25. The shipping portion 28 carries out the procedures for creating delivery slips and shipping receipts, for example, for supplying consumables to the medical institutions. The clock 29 is provided for acquiring the date and time information.

Here, an example of the data stored on the client inventory data memory portion 24 is shown. For each medical institution A, B, . . . , information on the consumables purchased from the consumables supplier C is stored on the client inventory data memory portion 24, separated into the test strip data shown in FIG. 4 and the non-test strip consumables data shown in FIG. 5.

Figure 4:
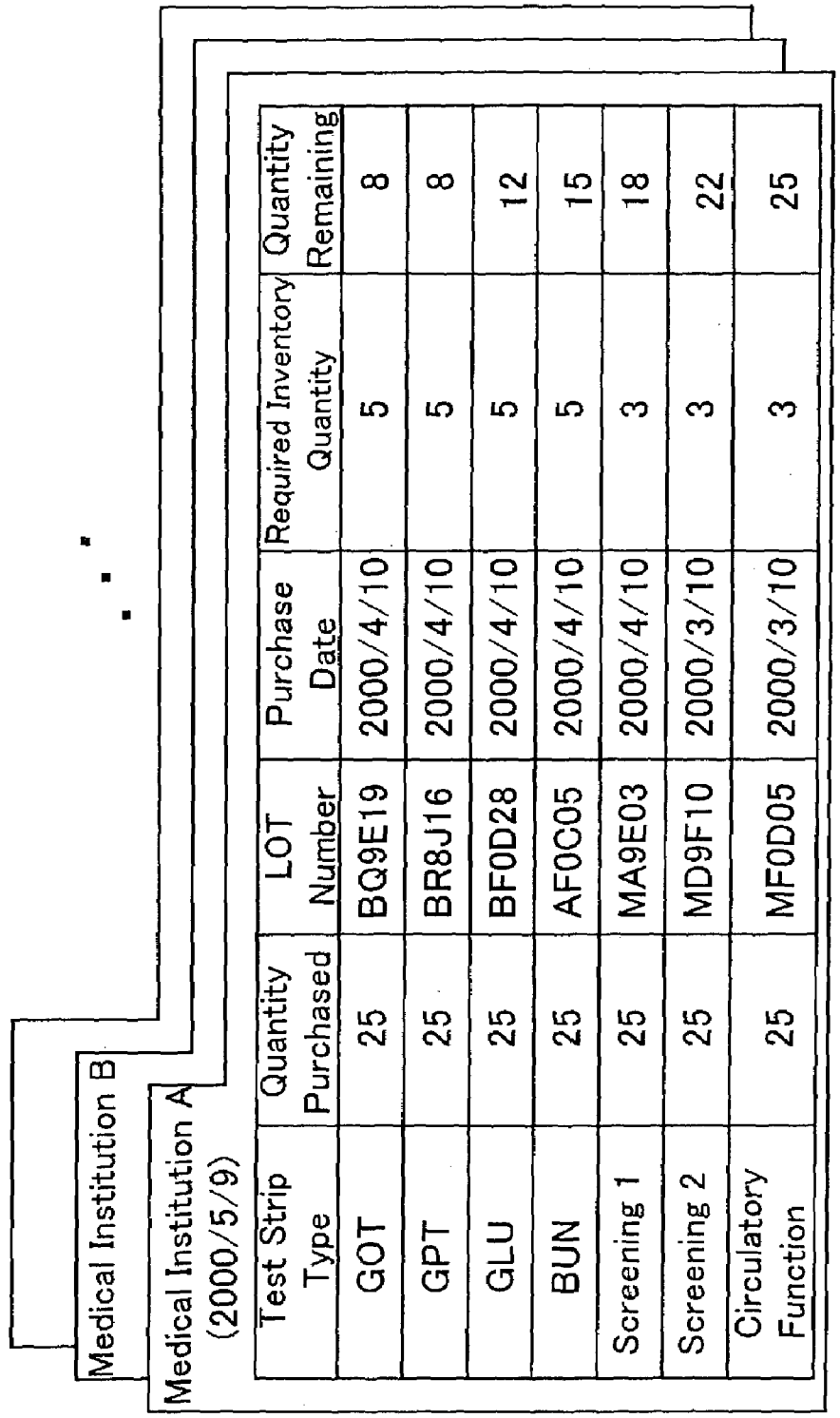
FIG. 4 is a diagram that schematically shows the structure of test strip data representing the purchase status of test strips in each medical institution, and shows an example of consumables inventory data recorded in the computer.

As shown in FIG. 4, the test strip data represents the purchase status of the test strips in each medical institution, and each time test strips are purchased by a medical institution from the consumables supplier C, the quantity purchased, the LOT number, the purchase date, the required inventory quantity, and the quantity remaining are input for each type of test strip.

For each type of consumable, an appropriate quantity is determined for the required inventory quantity mentioned above by taking into consideration records, for example, of past consumption by the medical institutions. Conversely, a suitable quantity also may be set by contract between the consumables supplier C and the medical institutions. The quantity remaining that is mentioned above is initially set to the value of the quantity purchased, and then, as described later, it is updated each time operation status data are transmitted from the clinical test analysis devices 1.

It should be noted that in the example of test strip data shown in FIG. 4, "GOT," "GPT," "GLU," and "BUN" in the column for test strip type represent single test strips for testing these items. On the other hand, "Screening 1," "Screening 2," and "Circulatory Function" represents different types of multiple test strips that are employed for these test applications.

Figure 5:
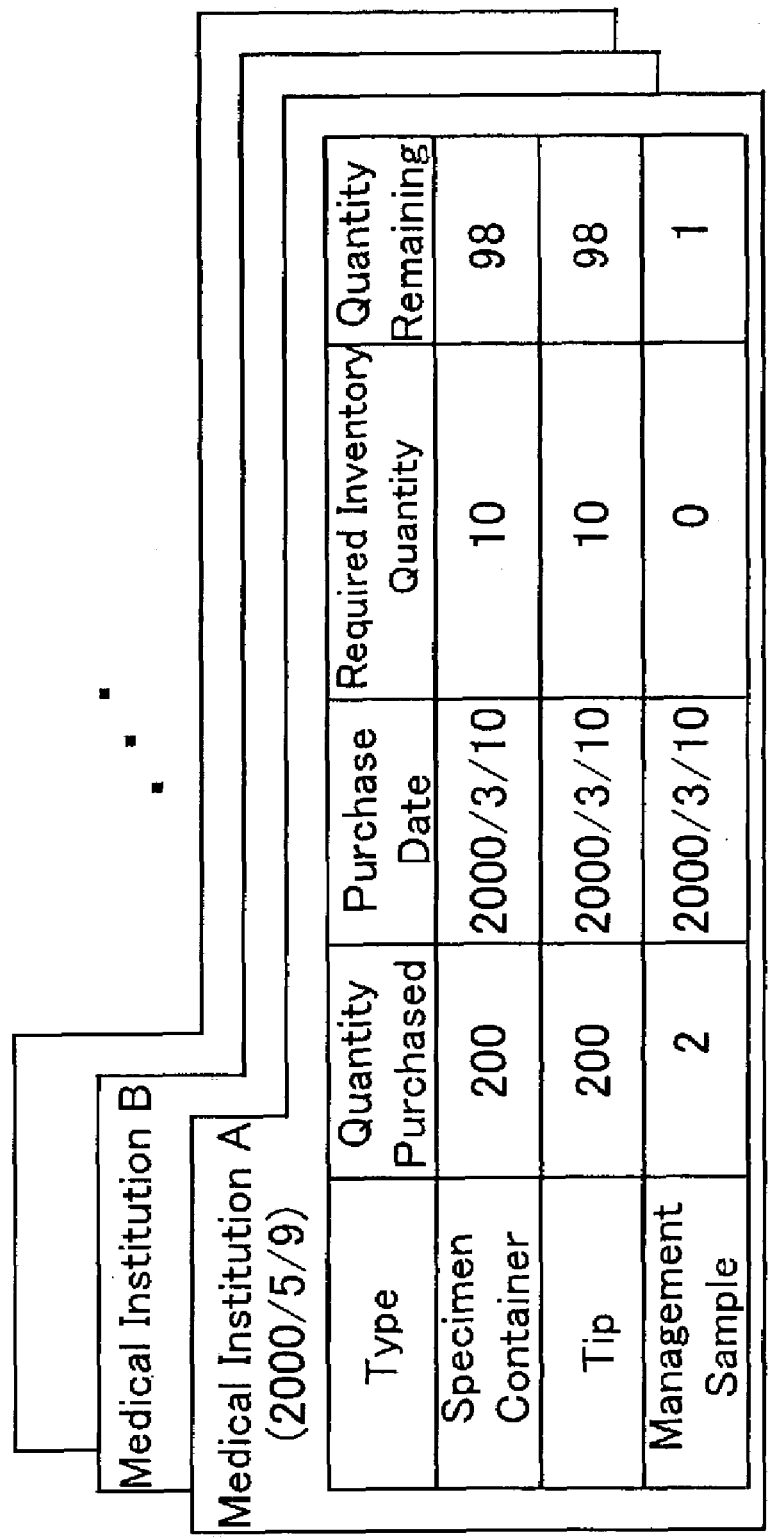
FIG. 5 is a diagram that schematically shows the structure of non-test strip consumables data representing the purchase status of consumables other than test strips in each medical institution, and shows an example of consumables inventory data recorded in the computer.

Also, as shown in FIG. 5, the non-test strip consumables data represent the purchase status of each medical institution for consumables other than test strips, namely specimen containers, tips (tip cartridges), and management samples, that are used in the clinical test analysis devices 1. For each type of item, the quantity purchased, the purchase date, the required inventory quantity, and the quantity remaining are stored for each of the medical institutions A, B, . . . on the client inventory data memory portion 24.

It should be noted that if a single medical institution has a plurality of clinical test analysis devices 1, then the combination of the test strip data and non-test strip consumables data for that number of units is stored in the client inventory data memory portion 24.

Next, the mechanism by which consumables are supplied to the clinical test analysis devices 1 in the present consumables supply system is described with reference to FIGS. 6 to 11.

First, the operation of the clinical test analysis devices 1 is described.

With the clinical test analysis devices 1, an operator starts measurement (selection of the measurement mode in step S1 of FIG. 6), and each time a measurement is performed by the measurement portion 12 (step S2), the control portion 11 acquires the date and time of measurement from the clock 18 (step S3) and obtains the type and LOT number of the test strips used in the measurement and also the number of measurements from the measurement portion 12 (step S4), and then, as shown in FIG. 7, stores these in the operation status memory portion 16 (step S5).

When the process of step S5 has ended normally, the control portion 11 returns control to step S1 of the procedure.

Also, the clinical test analysis devices 1, at a predetermined time, transmit data stored in the operation status memory portion 16 to the computer 2 of the consumables supplier 2 via the communications line 10. That is, when the control portion 11 detects that a predetermined time has been reached based on the date and time information obtained from the clock 18, it selects the transmission mode in step S1 and starts processing from step S6.

First, the control portion 11 sends a command to the communications control portion 17 to establish a connection with the computer 2 of the consumables supplier C via the communications line 10 (step S6). When a connection has been established, the control portion 11 retrieves the operation status data (date and time of measurements, type and LOT number of test strips used, number of measurements) from the operation status memory portion 16 (step S7), and transmits these data to the computer 2 from the communications control portion 17 (step S8).

When transmission of the operation status data to the computer 2 has ended normally, the control portion 11 makes the communications control portion 17 terminate connection (step S9), clears the contents of the operation status memory portion 16 (step S10), and returns control to step S1 of the procedure.

Next, the operation of the computer 2 of the consumables supplier C is described below. It should be noted that the computer 2 is capable of performing a variety of processes by reading and executing various application programs, although here, of the operations of the computer 2, only the process for receiving operation status data from the clinical test analysis device 1 (reception mode) and the process for performing the procedure for shipping required consumables to each medical institution (shipping mode) are described as the processes related to the supply of consumables.

First, the procedure of the operation in the reception mode is described.

Figure 6:
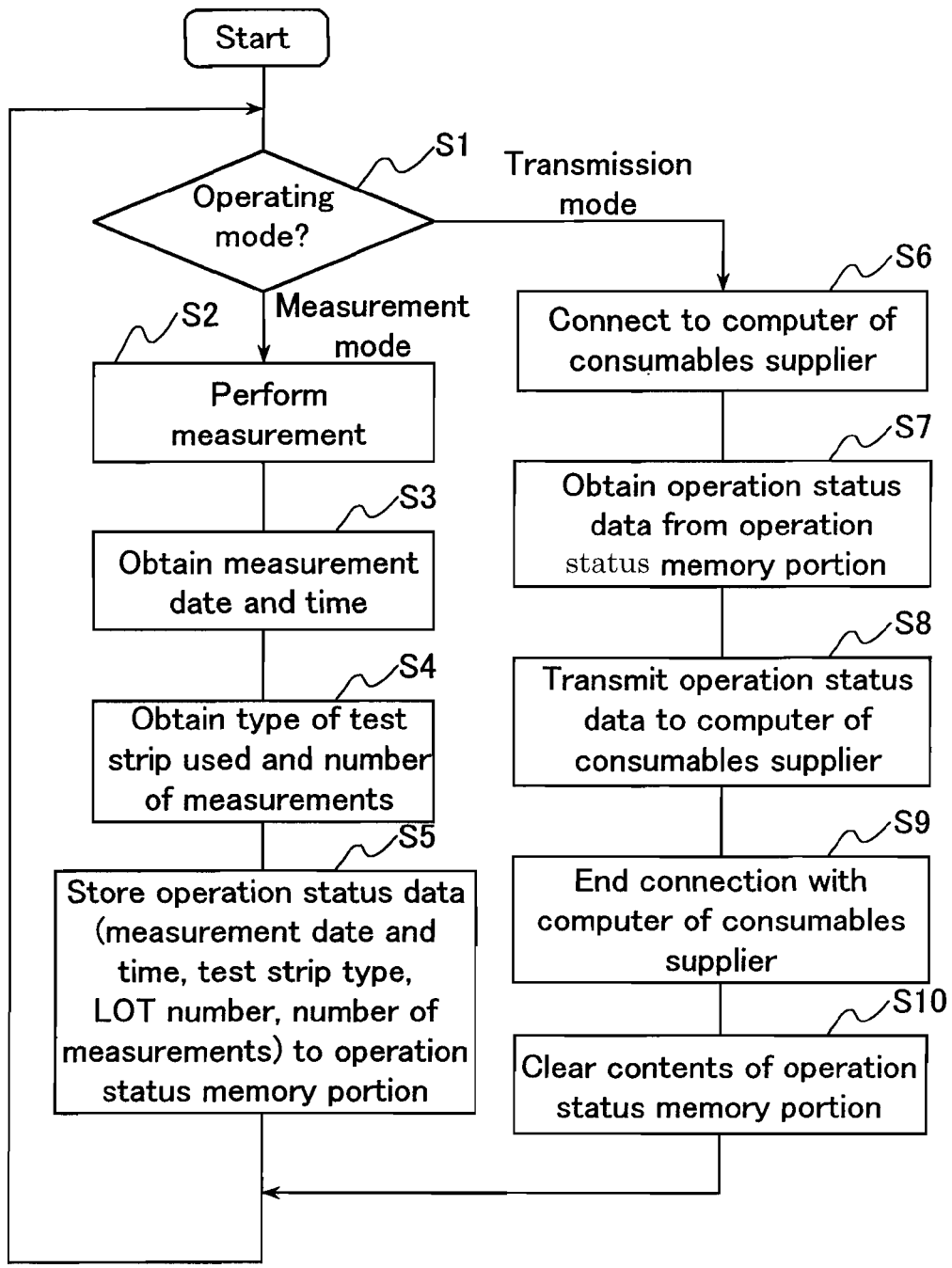
FIG. 6 is a flowchart showing the operation procedure of the clinical test analysis device.

The process of the reception mode is started by the control portion 21 when there has been a connection request for the transmission of operation status data from the clinical test analysis device 1 (step S6 in FIG. 6).

First, the control portion 21 uses the communications control portion 26 to respond to the connection request from the clinical analysis test device 1 and establish a connection between it and the clinical test analysis device 1 (step S12). Next, the control portion 21 makes the communications control portion 26 receive the operation status data that are transmitted from the clinical test analysis device 1 over the communications line 10 (step S13) and store the operation status data that are received in the temporary memory portion 27 (step 14). When the processes of steps S13 and S14 have ended normally, the control portion 21 makes the communications control portion 26 disconnect (step S15).

Next, the control portion 21 sends a command to the data processing portion 25 to determine the quantity of consumption of the consumables in the medical institution based on the operation status data stored in the temporary memory portion 27 (step S16).

Here, the process performed by the data processing portion in step S16 is described in detail under the premise that the operation status data shown in FIG. 7 have been received from the clinical test analysis device 1.

In the case of the operation status data shown in FIG. 7, there are thirteen data units, d1 to d13. The data processing portion 25 compares the measurement dates and times of the data, and if there are a plurality of data units in which the measurement date and time are identical, such as the combination of d1 and d2, the combination of d3 and d4, and the combination of d5 and d6, these plurality of data units are determined to be from measurements of an identical specimen.

That is, taking d1 and d2 as an example, these data units are determined to be the data from when measurement was performed by applying drops of a single specimen set in the specimen container onto a GPT test strip and a GOT test strip, respectively. Consequently, the number of consumables that were used when the measurements shown in d1 and d2 were performed is: one GPT test strip, one GOT test strip, one specimen container, and one tip. The same applies for the combination of d3 and d4 and the combination of d5 and d6.

As a result, the data processing portion 25 generates consumables consumption data like that shown in FIG. 9 from the operation status data shown in FIG. 7. It should be noted that in step S16, the standard for determining that a measurement has been made for the same specimen is not limited to whether the measurement date and time are identical, as in the case described above, and for example, taking into account the time required for a single measurement, for example, the standard can also be the condition of the difference in the measurement date and time between a plurality of data units being less than a predetermined time.

The consumables consumption data generated by the data processing portion 25 are sent to the consumption data memory portion 23 and stored (step S17). When the process of step S17 is ended normally, the control portion 21 returns control to step S11 in the procedure.

Next, the operation procedure of the shipping mode of the computer 2 is described.

The control portion 21 of the computer 2 starts processing from step S18 when a predetermined time is reached each day based on the date and time information obtained from the clock 29.

First, the control portion 21 sends a command to the data processing portion 25 to update the data stored in the client inventory data memory portion 24 for the clinical test analysis device 1 in the medical institution A based on the consumables consumption data stored in the consumption data memory portion 23 (step S18).

Figure 10:
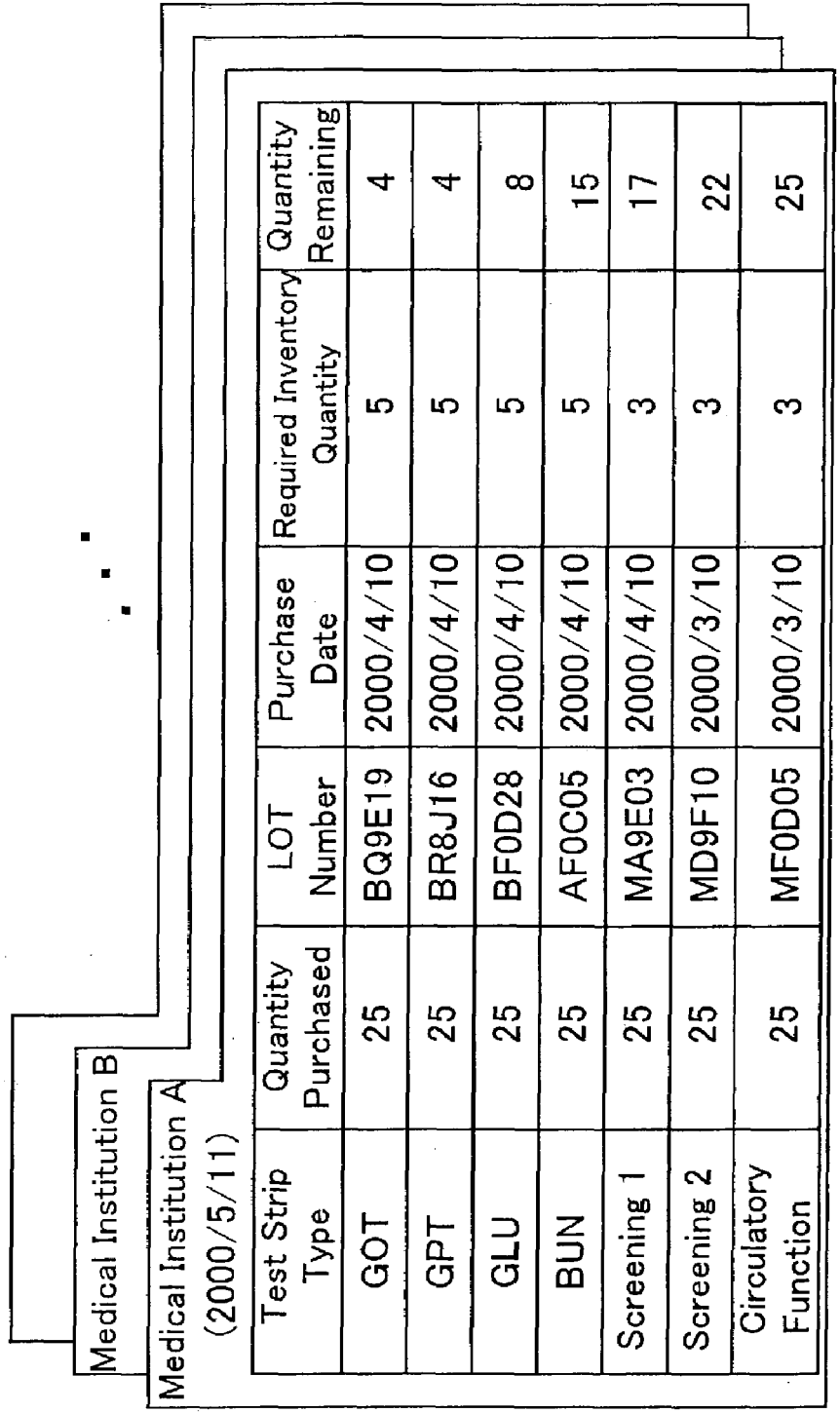
FIG. 10 is a diagram showing the results after updating the test strip data shown in FIG. 4 based on the consumables consumption quantity shown in FIG. 9.
Figure 11:
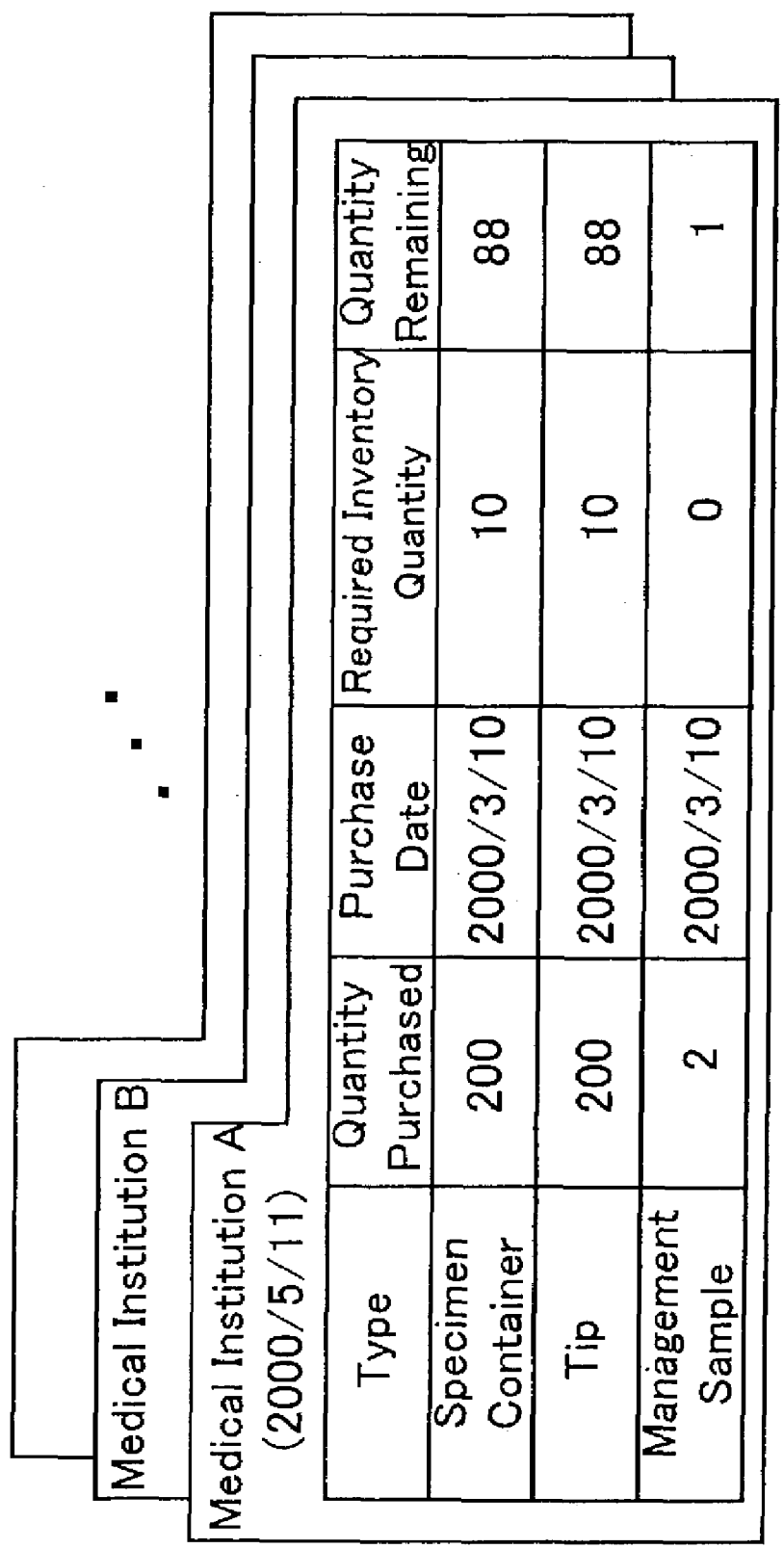
FIG. 11 is a diagram showing the results after updating the non-test strip consumables data shown in FIG. 5 based on the consumables consumption quantity shown in FIG. 9.

For example, if the consumables consumption data shown in FIG. 9 are used, then the test strip data shown in FIG. 4 and the non-test strip consumables data shown in FIG. 5 are updated as shown in FIG. 10 and FIG. 11 by subtracting the quantity of test strips, tips, specimen containers, and management samples that were consumed from the quantity remaining of each.

It should be noted that in step S18, if in the test strip data there are a plurality of records with different LOT numbers for consumables of the same type, then the quantity remaining is updated for each corresponding LOT number. In the non-test strip consumables data, in which there are no LOT numbers, if there are a plurality of records having different purchase dates for the same type of consumable item, then the quantity remaining after updating is calculated by regarding these as identical products and adding the two together.

In a case where the medical institution A has a plurality of clinical test analysis devices 1, the process of step S18 is carried out for all of the clinical test analysis devices 1.

Next, the control portion 21 sends a command to the data processing portion 25 to reference the updated test strip data and non-test strip consumables data and determine whether the remaining quantity of each consumable has fallen below the required inventory quantity in the medical institution A, that is, whether there are consumables that should be supplied (step S19).

For example, in the case of the test strip data of FIG. 10 and the non-test strip consumables data of FIG. 11, it is clear that the number of GOT test strips and GPT test strips remaining in the medical institution A is below the required inventory quantity.

In step S19, if in the test strip data there are a plurality of records with different LOT numbers for the same type of consumable, then the sum of the quantity remaining in these plurality of records is calculated, and whether to supply that consumable is then determined by comparing the sum that has been calculated and the required inventory quantity. Also, if in the non-test strip consumables data, in which there are no LOT numbers, there are a plurality of records in which the purchase date is different for the same type of consumable, then the sum of the quantity remaining in these plurality of records is calculated, and whether to supply that consumable is then determined by comparing the sum that has been calculated and the required inventory quantity.

If there are consumables to be supplied (YES in step S19), then the control portion 21 sends a command to the shipping portion 28 to carry out the shipping procedures so that a suitable quantity of those consumables is supplied (step S20).

It should be noted that the quantity of consumables supplied in step S20 can be determined suitably taking into account past consumption records, for example, for that consumable in that medical institution. Conversely, an appropriate quantity can be agreed upon in advance by contract between the consumables supplier C and each medical institution.

The control portion 21 determines whether the shipping has been carried out for all medical institutions after the process of step S20 has ended for the medical institution A (step S21), and until the result determined in step S21 becomes YES, the control portion 21 selects medical institutions for which shipping has not yet been performed (step S22), and repeats the processes of steps S18 to S20.

When the shipping of step S20 is complete for all medical institutions, data on the consumables that were shipped are added to the client inventory data memory portion 24. This additional input can be performed manually by an operator of the computer 2 based on the shipping receipts, for example, or can be automatically input from an outside system in connection with an inventory management system or the like inside the consumables supplier C.

If in the shipping procedure of step S20 the same consumable is delivered to the medical institution A and the medical institution B, for example, then it is also possible to compare the speed at which that consumable is consumed in these medical institutions, and if the speed of consumption for that consumable is sufficiently higher in one medical institution than in the other, then consumables with a close expiration date can be selected and shipped to the medical institution with the higher consumption speed.

Thus, the consumables supply system according to this embodiment allows the stock of consumables always to be maintained at or above a predetermined amount, even without a user (medical institution) of the clinical test analysis device 1 managing the inventory of and placing orders for consumables, for example, and obviates impediments to testing caused by stock shortages. Also, it allows the consumables suppliers to readily create their production schedule because predicting demand is easy, and reduce distribution costs by optimizing their inventory of consumables.

It should be noted that in the above description, each clinical test analysis device 1 transmitted data on its operation status at predetermined times. However, there is no limit to this, and it is also possible for transmission to be performed when a predetermined number of data units has accumulated in the operation status memory portion 16 of the clinical test analysis device 1. Conversely, data also may be transmitted each time a measurement is made by the clinical test analysis device 1.

Also, instead of each clinical test analysis device 1 automatically transmitting operation status data, it is also possible for the computer 2 to periodically send a data transmission request to each clinical test analysis device 1 and for the clinical test analysis devices 1 to transmit their operation status data in correspondence with that data transmission request.

Moreover, in the above description, an example was shown in which the communications control portion 17 of the clinical test analysis device 1 and the communications control portion 26 of the computer 2 are directly connected via the communications line 10. However, the method of communication between the clinical test analysis devices 1 and the computer 2 is not limited to a direct connection, and may also be achieved via the Internet (via the server of a provider), for example.

Also, in this embodiment, in step S19 the control portion 21 of the computer 2 makes the data processing portion 25 determine whether it is necessary to supply consumables, and if it is necessary, then in step S20 it makes the shipping portion 28 carry out the shipping procedures. However, it is not absolutely necessary that the computer 2 execute the shipping procedures as well, and for example, it is also possible to adopt a system in which the processes up to step S19 are executed by the computer 2 and the procedures for shipping the consumables are managed by a human, or conversely, a system in which another computer or the like that operates independently of the computer 2 carries out the shipping procedures.

Furthermore, in this embodiment, the data processing portion 25 carried out both the process for updating the consumables inventory data and the process for determining whether it is necessary to supply consumables to a user based on the updated consumables inventory data. However, in an alternative configuration, it is also possible for an independent block to be provided to carry out the latter process or for the shipping portion 28 to execute the latter process.

Second Embodiment

Another embodiment of the invention is described below.

The consumables supply system of this embodiment differs from the system of the first embodiment in that the shipping portion 28 in the computer 2 of the consumables supplier C adjusts the quantity of consumables supplied to each medical institution considering seasonal fluctuations in the consumption of consumables. Here, an example of a measurement device for which seasonal fluctuations in consumable consumption is particularly noticeable is a urinary analysis device.

That is, a urinary analysis device can be adopted as the clinical test analysis device 1 in the consumables supply system of this embodiment. It should be noted that a urinary analysis device according to this embodiment differs from the clinical test analysis device 1 that was described in the first embodiment only in that the structure and operation of the measurement portion 12 has been specialized for urinary analysis, and because the configuration and the operation of the functional blocks other than the measurement portion 12 are substantially the same as those of the first embodiment, they will not be described in detail here. Examples of consumables that are used in this urinary analysis device include test strips for outpatient testing and two types of test paper for general examination.

Figure 12:
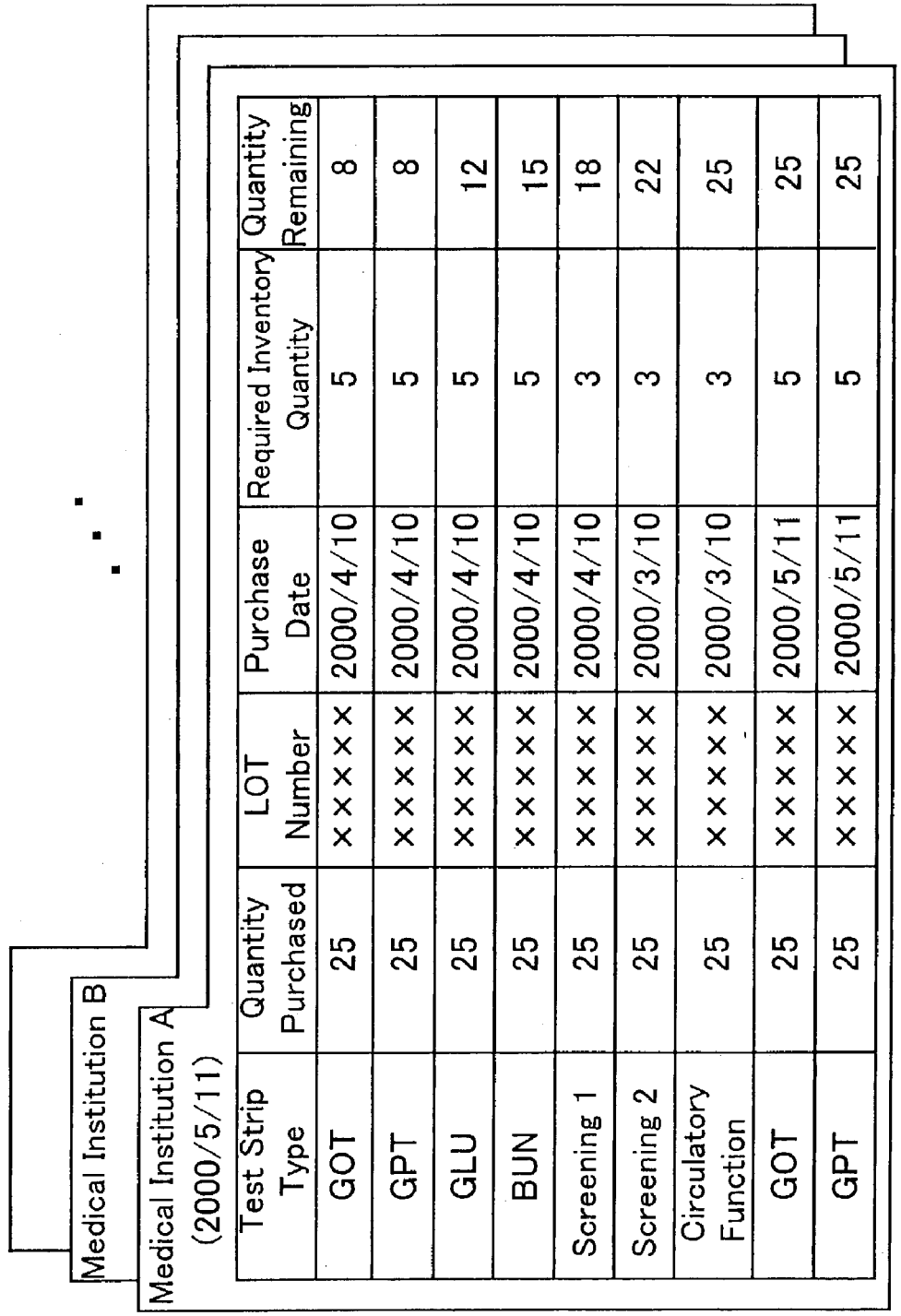
FIG. 12 is a graph showing the monthly consumables consumption quantities for a urinary analysis device that is used as the measurement device in another embodiment of the invention.

Here, the seasonal fluctuation in consumables consumption by the urinary analysis device is shown in FIG. 12. As is apparent from FIG. 12, the number of test strips for outpatient testing remains substantially constant throughout the year, whereas the number of test papers for general examination that are consumed noticeably increases in the months where there is a large number of health check-ups (particularly May).

Figure 8:
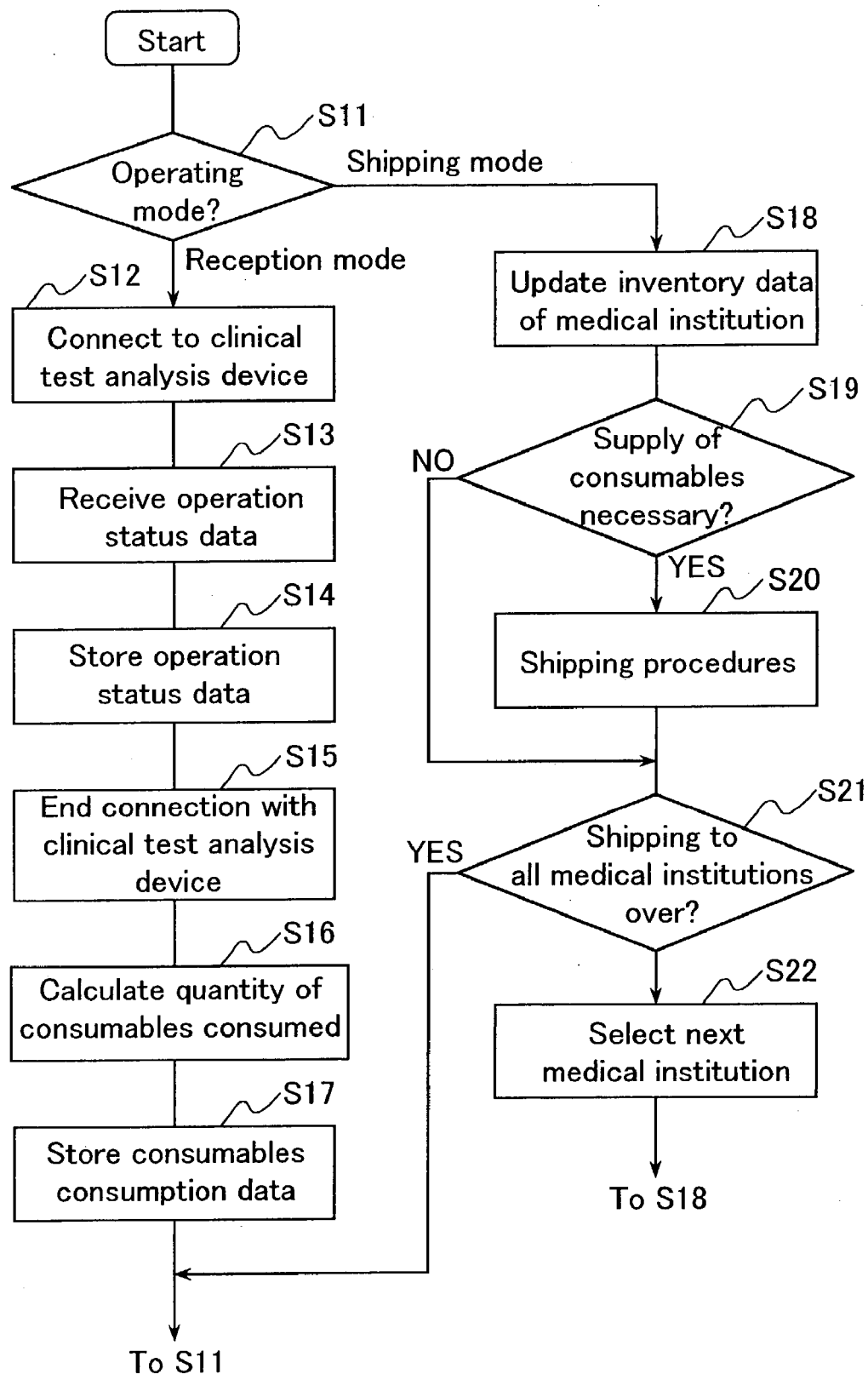
FIG. 8 is a flowchart showing the operation procedure of the computer.

Consequently, the shipping portion 28 in the computer 2 of the consumables supplier C according to this embodiment, in the shipping procedure of step S20 of FIG. 8, adjusts the quantity of test papers for general examination that is supplied to each medical institution to correspond to the monthly fluctuations in consumption, such as shown in FIG. 12.

Thus, testing in the medical institutions is not adversely affected by shortages in the stock of consumables, even during periods when large quantities of consumables are used. Also, consumables suppliers readily can set their production schedule because predicting demand is easy, and they also can optimize the quantity of stocked consumables and lower distribution costs.

The above-described embodiments are not to be construed as limiting of the invention, and various alterations are possible within the scope of the invention. For example, the types of consumables are not limited to those specifically mentioned in the embodiments. Also, the measurement device is not limited to only medical applications.

INDUSTRIAL APPLICABILITY

As described in the foregoing, the present invention provides a consumables supply management system that allows a required and adequate stock of consumables to always be secured, even without a user of a measurement device managing the inventory of and placing orders for consumables, for example, and also allows consumables suppliers to reduce distribution costs by optimizing their quantity of inventory.

The invention claimed is:

1. A consumables supply management device that is connected via a communications line to a measurement device using consumables and that manages a supply of consumables for a user of the measurement device, wherein operation status data including information on a consumption status of consumables is generated in the measurement device, the consumables supply management device comprising:
    an inventory data memory portion for storing consumables inventory data including information on an inventory status of consumables for a user of the measurement device;
    a data reception portion for receiving the operation status data from the measurement device via the communications line;
    a data processing portion that determines a quantity of consumables consumed by the measurement device based on the operation status data received by the data reception portion, and updates the consumables inventory data in the inventory data memory portion; and a supply determining portion for determining whether it is necessary to supply consumables to the user of the measurement device based on the consumables inventory data updated by the data processing portion;
    wherein the measurement device is a clinical test analysis device that uses one unit of the consumables per one specimen obtained from a test subject to perform an analysis of the specimen;
    wherein the operation status data include a measurement time for each of a plurality of measurements conducted by the measurement device; and
    wherein when a difference in the measurement times of the plurality of measurements is within a predetermined time, the data processing portion determines that the plurality of measurements are measurements in which an identical specimen was used, and determines the quantity of the consumables consumed in the plurality of measurements as the one unit.

2. The consumables supply management device according to claim 1, further comprising a supply processing portion that carries out a procedure for supplying consumables to the user if the supply determining portion determines that it is necessary to supply those consumables.

3. The consumables supply management device according to claim 1, wherein an inventory quantity of the consumables required by the user of the measurement device is predetermined, and
    the supply determining portion determines whether it is necessary to supply consumables to the user of the measurement device by comparing an inventory quantity of the consumables updated by the data processing portion with the required inventory quantity.

4. The consumables supply management device according to claim 2, wherein the supply processing portion sets the quantity of consumables supplied to the user to a quantity predetermined for that user.

5. The consumables supply management device according to claim 2, wherein the supply processing portion determines the quantity of consumables supplied to the user from a record of consumption of the consumables by that user.

6. The consumables supply management device according to claim 2, wherein the supply processing portion determines the quantity of consumables supplied to the user in correspondence with temporal fluctuations in the quantity of the consumables consumed.

7. The consumables supply management device according to claim 2, wherein when the supply processing portion carries out procedures for supplying the same type of consumable to a plurality of users, procedures are performed to supply a lot having a closer expiration date to a user that consumes a larger quantity of the consumable rather than to a user that consumes a smaller quantity.

8. The consumables supply management device according to claim 1, wherein one unit of the specimen consumable includes at least one of a specimen container and a sampling tip.

9. A consumables supply management system in which a measurement device that uses consumables and a consumables supply management device for managing supply of consumables for a user of the measurement device are connected via a communications line, and comprises:
    an operation status memory portion for storing operation status data including information on a consumption status of the consumables; and
    a data transmission portion for transmitting the operation status data to the consumables supply management device via the communications line; and
    wherein the consumables supply management device comprises:
        an inventory data memory portion for storing consumables inventory data including information on an inventory status of consumables for a user of the measurement device;
        a data reception portion for receiving the operation status data from the measurement device via the communications line;
        a data processing portion that determines a quantity of consumables consumed by the measurement device based on the operation status data received by the data reception portion, and updates the consumables inventory data in the inventory data memory portion; and a supply determining portion for determining whether it is necessary to supply consumables to the user of the measurement device based on the consumables inventory data updated by the data processing portion;

wherein the measurement device is a clinical test analysis device that uses one unit of the consumables per one specimen obtained from a test subject to perform an analysis of the specimen;

wherein the operation status data include a measurement time for each of a plurality of measurements conducted by the measurement device; and wherein when a difference in the measurement times of the plurality of measurements is within a predetermined time, the data processing portion determines tat the plurality of measurements are measurements in which an identical specimen was used, and determines the quantity of the consumables consumed in the plurality of measurements as the one unit.

10. The consumables supply management system according to claim 9, wherein the consumables supply management device further comprises a supply processing portion that carries out a procedure for supplying consumables to the user if the supply determining portion determines that it is necessary to supply consumables.

11. The consumables supply management system according to claim 9, wherein an inventory quantity of the consumables required by the user of the measurement device is predetermined, and the supply determining portion of the consumables supply management device determines whether it is necessary to supply consumables to the user of the measurement device by comparing an inventory quantity of the consumables updated by the data processing portion and the required inventory quantity.

12. The consumables supply management system according to claim 10, wherein the supply processing portion of the consumables supply management device sets the quantity of consumables supplied to the user to a quantity predetermined for that user.

13. The consumables supply management system according to claim 10, wherein the supply processing portion of the consumables supply management device determines the quantity of consumables supplied to the user from a record of consumption of the consumables by that user.

14. The consumables supply management system according to claim 10, wherein the supply processing portion of the consumables supply management device determines the quantity of consumables supplied to the user in correspondence with temporal fluctuations in the quantity of the consumable that is consumed.

15. The consumables supply management system according to claim 10, wherein when the supply processing portion of the consumables supply management device carries out procedures For supplying the same type of consumable to a plurality of users, procedures are performed to supply a lot having a closer expiration date to a user that consumes a larger quantity of the consumable rather than to a user that consumes a smaller quantity.

16. The consumables supply management system according to claim 9, wherein one unit of the specimen consumable includes at least one of a specimen container and a sampling tip.

17. A program storage medium on which is stored a program for controlling operation of a consumables supply management device that is connected via a communications line to a measurement device using consumables, and that manages supply of consumables for a user of the measurement device, the program executing the processes of:

receiving operation status data, including a measurement time for each of a plurality of measurements conducted by the measurement device, from the measurement device via the communications line;

determining a consumed quantity of consumables in the measurement device based on the operation status data that are received;

updating consumables inventory data in an inventory data memory portion that stores the consumables inventory data including information on an inventory status of consumables for the user of the measurement device; and determining whether it is necessary to supply consumables to the user of the measurement device based on the updated consumables inventory data;

wherein in determining the consumed quantity of the consumable when a difference in the measurement tines of a plurality of measurements is within a predetermined time, the plurality of measurements are measurements in which an identical specimen was used is determined and the quantity of the consumable consumed in the plurality of measurements as the one unit is determined; and wherein the measurement device is a clinical test analysis device that uses one unit of the consumables per one specimen obtained from a test subject to perform an analysis of the specimen.

* * * * *